United States Patent
Samain

(10) Patent No.: US 9,326,931 B2
(45) Date of Patent: *May 3, 2016

(54) USE OF PORPHYRIN-TYPE CATALYTIC OXIDATION COMPOUNDS AS AN ANTI-DANDRUFF AGENT

(71) Applicant: L'OREAL, Paris (FR)

(72) Inventor: Henri Samain, Bievres (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/381,741

(22) PCT Filed: Feb. 22, 2013

(86) PCT No.: PCT/FR2013/050360
§ 371 (c)(1),
(2) Date: Oct. 10, 2014

(87) PCT Pub. No.: WO2013/128101
PCT Pub. Date: Sep. 6, 2013

(65) Prior Publication Data
US 2015/0064120 A1    Mar. 5, 2015

Related U.S. Application Data

(60) Provisional application No. 61/728,269, filed on Nov. 20, 2012.

(30) Foreign Application Priority Data

Feb. 29, 2012    (FR) ...................................... 12 51836

(51) Int. Cl.
| | |
|---|---|
| *A61Q 5/06* | (2006.01) |
| *A61K 8/58* | (2006.01) |
| *A61K 8/49* | (2006.01) |
| *A61Q 5/00* | (2006.01) |
| *A61K 8/19* | (2006.01) |
| *A61Q 17/04* | (2006.01) |
| *A61Q 7/00* | (2006.01) |

(52) U.S. Cl.
CPC ... *A61K 8/58* (2013.01); *A61K 8/19* (2013.01); *A61K 8/494* (2013.01); *A61Q 5/006* (2013.01); *A61Q 17/04* (2013.01); *A61K 2800/58* (2013.01); *A61K 2800/75* (2013.01); *A61Q 7/00* (2013.01)

(58) Field of Classification Search
CPC ....... A61Q 5/006; A61K 8/27; A61K 8/4906; A61K 8/494; A61K 2800/58
USPC ....................................................... 424/70.1
See application file for complete search history.

(56) References Cited

U.S. PATENT DOCUMENTS

| | | |
|---|---|---|
| 5,202,317 A | 4/1993 | Bruice |
| 7,429,275 B2 * | 9/2008 | Hercouet et al. .................. 8/405 |
| 2003/0050296 A1 | 3/2003 | Bommer et al. |
| 2003/0153546 A1 | 8/2003 | Schaffer et al. |
| 2005/0214075 A1 * | 9/2005 | Reedijk et al. .................. 405/29 |
| 2012/0016289 A1 | 1/2012 | Prestwich et al. |

OTHER PUBLICATIONS

STIC Search Report dated Dec. 14, 2014.*
French International Search Report for PCT/FR2013/050360, (2013).
Translation of International Search Report for PCT/FR2013/050360, (2013).
Bristow, C.A. et al., "Potential of Cationic Porphyrins for Photodynamic Treatment of Cutaneous Leishmaniasis," Photodiagnosis and Photodynamic Therapy, vol. 3, No. 3, (Sep. 1, 2006), pp. 162-167.
Mikolajewska, Patrycja et al., "Microneedle Pre-Treatment of Human Skin Improves 5-Aminolevulininc Acid Methyl Ester (MAL)-Induced PpIX Production for Topical Photodynamic Therapy Without Increase in Pain or Erythema," Pharmaceutical Research, vol. 27, No. 10, (Jul. 31, 2010), pp. 2213-2220.

* cited by examiner

*Primary Examiner* — Elsa Elhilo
(74) *Attorney, Agent, or Firm* — The Marbury Law Group, PLLC

(57) ABSTRACT

The present invention relates to the cosmetic use, as an anti-dandruff agent, of catalytic oxidation compounds chosen from porphyrins, or of a cosmetic composition comprising the same.

8 Claims, No Drawings

USE OF PORPHYRIN-TYPE CATALYTIC OXIDATION COMPOUNDS AS AN ANTI-DANDRUFF AGENT

CROSS REFERENCE TO RELATED APPLICATIONS

This is a national stage application of PCT/FR2013/050360, filed internationally on Feb. 22, 2013, which claims priority to U.S. Provisional Application No. 61/728,269, filed on Nov. 20, 2012, as well as French Application No. FR 1251836, filed on Feb. 29, 2012, all of which are incorporated herein by reference in their entireties.

The present invention relates to the cosmetic use of particular catalytic oxidation compounds as antidandruff agents, in particular in the cosmetic treatment of dandruff conditions associated with the excessive proliferation of yeasts of the *Malassezia* genus on the scalp. The invention also relates to a cosmetic treatment process for eliminating and/or reducing dandruff, especially that caused by yeasts of the *Malassezia* genus, which employs the said compounds.

Dandruff problems affect up to 50% of the worldwide population. They affect both men and women and are perceived as having a very negative psychosocial impact. The appearance of dandruff is disagreeable both aesthetically and because of the irritation it causes (especially itching), and as such many people confronted with this problem to variable degrees wish to eliminate it efficiently and permanently.

Dandruff corresponds to excessive and visible desquamation of the scalp resulting from excessively rapid multiplication of the epidermal cells and their abnormal maturation. This phenomenon may be caused especially by excessively aggressive hair treatments, extreme climatic conditions, nervousness, the diet, fatigue and pollution.

Dandruff conditions usually result from a disorder of the scalp microflora, and more particularly from excessive colonization of a fungus which belongs to the family of yeasts of the genus *Malassezia* and which is naturally present on the scalp.

Many antidandruff treatments have been developed with the principal objective of eradicating scalp *Malassezia* yeasts. Thus, the activity of the antidandruff agents currently used, such as zinc pyrithione, piroctone olamine or selenium disulfide, is based mainly on their fungicidal property. However, these antidandruff agents are not completely satisfactory in terms of effectiveness (immediate effectiveness or duration of the effect) and/or in terms of impact on the environment.

The aim of the present invention is to provide antidandruff agents that are non-irritant to the skin and the scalp, and that are as effective as the known antidandruff agents, while at the same time having a more favourable environmental impact (low bioaccumulation and good biodegradability in particular). The aim of the invention is also to propose active agents that can re-establish the ecoflora of the scalp and especially prevent excessive colonization of the scalp by *Malassezia* sp.

The Applicant has now found, surprisingly, that the use of at least one particular catalytic oxidation compound makes it possible to effectively treat dandruff conditions, in particular those associated with the proliferation of yeasts of the *Malassezia* genus, and to overcome the drawbacks of the prior art.

It has been observed that, by using the compounds according to the invention, it is possible to eliminate and/or reduce the number of yeasts of the *Malassezia* genus, the number of dandruff flakes, and also the itching and redness on the scalp. One subject of the present invention is thus the cosmetic use of at least one catalytic oxidation compound chosen from the porphyrins of formula (I) described below, or a cosmetic composition comprising the same, as antidandruff agent.

In the present invention, the term "keratin material" especially means the skin (of the face, body or scalp), the hair, the eyelashes, the eyebrows and the nails.

For the purposes of the present invention, the term "catalytic oxidation compound chosen from porphyrins" means porphyrin compounds that have catalytic oxidation properties.

The catalytic oxidation porphyrin compounds used according to the invention differ from porphyrin compounds that do not have catalytic oxidation properties by at least one of the three tests as described below.

Test 1: Oxidation of 2,2,6,6-tetramethylpiperidine (TEMP)

In this test, the compound 2,2,6,6-tetramethylpiperidine (TEMP) sold by the company Sigma Aldrich acts as a probe revealing the catalytic activity of a porphyrin compound as oxidation catalyst. The oxidizing agent used in this test is dissolved oxygen.

A solution comprising a phosphate buffer (pH 7.4), 50 mM of the compound 2,2,6,6-tetramethylpiperidine (TEMP) and a porphyrin compound at 0.5 µM is prepared. The solution is saturated with oxygen. The solution is placed in daylight. After 1 hour, electron paramagnetic resonance (EPR) spectrometry of the oxidized form of the compound 2,2,6,6-tetramethylpiperidine (TEMP), which corresponds to the compound (2,2,6,6-tetramethylpyridin-1-yl)oxyl, known as TEMPO, is performed.

In accordance with the scientific publication Lion et al., 1976; Moan and Wold, 1979, the presence of the compound in TEMPO form is indicative of the oxidation produced by oxygen on the compound 2,2,6,6-tetramethylpiperidine and thus of the catalytic effect of the porphyrin compound.

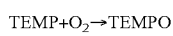

$$TEMP + O_2 \rightarrow TEMPO$$

More specifically, the spectrum shows three peaks of equivalent intensity characteristic of the presence of the nitroxide radical in the TEMPO oxidized form. With a porphyrin compound according to the invention, the appearance of the TEMPO compound is observed after 1 hour of placing in contact.

Conversely, the presence of a porphyrin that is not included in the invention, for instance copper chlorophyllin, does not lead to the formation of the TEMPO compound.

Test 2: Oxidation of DMPO

In this test, the compound 5,5-dimethyl-1-pyrroline N-oxide (DMPO) acts as a probe revealing the catalytic activity of a porphyrin compound as oxidation catalyst. The oxidizing agent used in this test is dissolved oxygen.

An aqueous solution of pH 7 comprising 100 mM of DMPO and a porphyrin compound at 100 µM is prepared. The solution is saturated with oxygen. The solution is placed in daylight.

After 1 hour, electron paramagnetic resonance (EPR) spectrometry of the oxidized form of the compound 5,5-dimethyl-1-pyrroline N-oxide, known as DMPO-OH, is performed. The presence of the DMPO-OH form is indicative of the oxidation of the compound 5,5-dimethyl-1-pyrroline N-oxide and, consequently, of the catalytic activity of the porphyrin compound.

More precisely, the EPR spectrum is characterized by a constant (hyperfine coupling constant) of $a^N = a^H = 14.6$ G.

Test 3: Activation of Hydrogen Peroxide 1 mM of a porphyrin compound is placed in 10-volumes aqueous hydrogen peroxide solution, of spontaneous pH. The solution is placed in daylight. The hydrogen peroxide content is then assayed.

The porphyrin compound is considered to be a catalytic oxidizing agent if it reduces the amount of hydrogen peroxide by a factor of at least 2 (5 volumes or less at the end).

The catalytic oxidation porphyrin compounds according to the invention satisfy at least one of the three tests mentioned above.

The catalytic oxidation compounds in accordance with the present invention may be cationic, anionic or nonionic.

Preferably, the catalytic oxidation porphyrin compounds are chosen from symmetrical porphyrin compounds.

The term "symmetrical porphyrin compounds" means porphyrin compounds for which, firstly, the radicals located in the meso position are identical (to each other), and, secondly, the radicals located in the beta-pyrrole position are also identical (to each other).

In other words, in accordance with the nomenclature described below, the fact that the radicals located in the meso position are identical means that the radicals located in the alpha position are identical. Furthermore, the fact that the radicals located in the beta-pyrrole position are identical means that the radicals located, firstly, in positions 1, 3, 5 and 7 are identical, and, secondly, that the radicals located in positions 2, 4, 6 and 8 are identical.

The nomenclature of the porphyrin compound is recalled below.

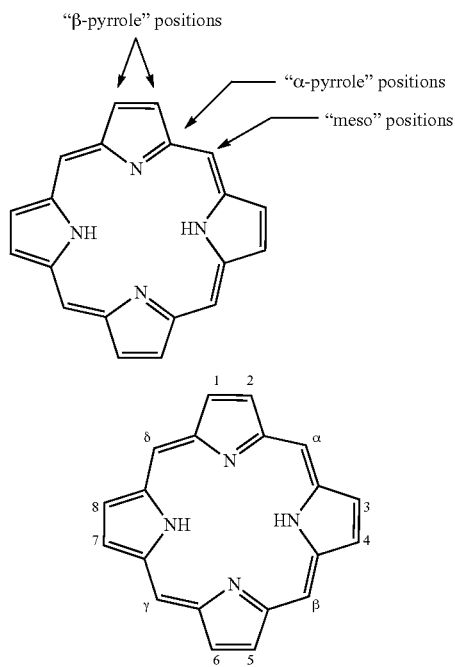

Preferably, the catalytic oxidation porphyrin compounds are chosen from cationic porphyrin compounds, i.e. porphyrin compounds in which the groups placed in the meso or beta-pyrrole position are cationic.

The catalytic oxidation compounds according to the invention correspond to formula (I) below:

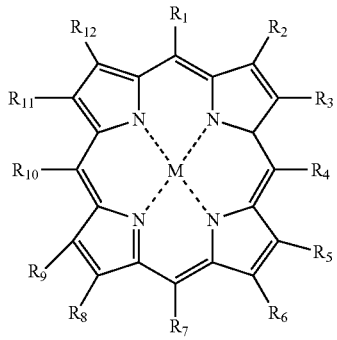

in which:

$R_2$, $R_3$, $R_5$, $R_6$, $R_8$, $R_9$, $R_{11}$ and $R_{12}$, which may be identical or different, represent a hydrogen atom; a linear or branched $C_1$-$C_{30}$ alkyl radical, which may be interrupted with one or more groups containing heteroatoms and/or which may be substituted; a linear or branched $C_2$-$C_{30}$ alkenyl radical, which may be interrupted with one or more groups containing heteroatoms and/or which may be substituted; a linear or branched $C_2$-$C_{30}$ alkynyl radical, which may be interrupted with one or more groups containing heteroatoms and/or which may be substituted;

$R_2$ and $R_3$, $R_5$ and $R_6$, $R_8$ and $R_9$ and/or $R_{11}$ and $R_{12}$ also possibly forming, respectively, with the carbon atoms that bear them, an optionally substituted aryl ring, preferably phenyl;

$R_1$, $R_4$, $R_7$ and $R_{10}$, which may be identical or different, represent a cationic group such as an optionally substituted pyridinium group; an anionic group such as a phenyl radical substituted with a group $SO_3M'$- with M' denoting a hydrogen atom or a cation derived, for example, from a metal or an amine or an ammonium cation; a linear or branched $C_8$-$C_{30}$ alkyl radical, which may be interrupted with one or more groups containing heteroatoms and/or which may be substituted; a reactive group, which may be chosen from siloxanes, esters and compounds comprising one or more thiol groups; as defined, for example, in the article Synthesis of "Porphyrin-Linker-Thiol" Molecules with Diverse Linkers for Studies of Molecular-Based Information Storage>>, by Daniel T. Gryko, Christian Clausen, Kristian M. Roth, Narasaiah Dontha, David F. Bocian, Werner G. Kuhr, Jonathan S. Lindsey, in the scientific publication J. Org. Chem. 2000, 65, 7345-7355;

M is a metal, or a metal ion, chosen from transition metals and alkaline-earth metals.

In the context of the definitions of the groups $R_1$, $R_2$, $R_3$, $R_4$, $R_5$, $R_6$, $R_7$, $R_8$, $R_9$, $R_{10}$, $R_{11}$ and $R_{12}$, the term "substituted" means substituted with one or more radicals chosen from the following radicals: i) hydroxyl, ii) $C_1$-$C_4$ alkoxy, iii) acylamino, iv) a halogen atom, preferably chlorine; v) amino optionally substituted with one or two identical or different $C_1$-$C_{10}$ alkyl radicals, the said alkyl radicals possibly forming, with the nitrogen atom that bears them, a 5- to 7-membered heterocycle, optionally comprising another nitrogen or non-nitrogen heteroatom; v) an optionally substituted 5- or 6-membered heterocycle, comprising one or more heteroatoms such as oxygen or nitrogen, optionally bearing at least one cationic charge.

In the context of the definitions of the groups $R_1$, $R_2$, $R_3$, $R_4$, $R_5$, $R_6$, $R_7$, $R_8$, $R_9$, $R_{10}$, $R_{11}$ and $R_{12}$, the term "interrupted with one or more groups containing heteroatoms" means interrupted with one or more groups chosen from an oxygen or sulfur atom; an imino group; an imino group substituted with a linear or branched $C_1$-$C_{10}$ alkyl radical, optionally bearing one or more hydroxyl or linear or branched $C_1$-$C_{10}$ alkoxy groups; an imino group substituted with two identical or different linear or branched $C_1$-$C_{10}$ alkyl radicals, optionally bearing one or more hydroxyl or linear or branched $C_1$-$C_{10}$ alkoxy groups; a carbonyl group; an optionally substituted 5- or 6-membered heterocycle, comprising one or more heteroatoms such as oxygen or nitrogen, optionally bearing at least one cationic charge.

In this formula (I), the metal M is linked to the nitrogen atoms forming the pyrrole rings via covalent bonds.

M is a metal, or a metal ion, chosen from transition metals and alkaline-earth metals, preferably transition metals.

The term "alkaline-earth metal" means metals from column IIA of the Periodic Table of the Elements, and especially magnesium (Mg) and calcium (Ca).

The term "transition metal" means metals from columns IB, IIB, IIIB, IVB, VB, VIB and VIIB and from the three columns VIII of the Periodic Table of the Elements. Preferably, the transition metals are chosen from those from column IB, especially copper, from column IIB, especially zinc (Zn), from column VIIB, especially manganese (Mn), and from the columns VIII, especially iron (Fe) and cobalt (Co). Preferentially, the metal M is chosen from zinc, manganese, iron, cobalt, magnesium and calcium, and more preferentially the metal M is zinc.

In accordance with one embodiment, $R_2$ and $R_3$, $R_5$ and $R_6$, $R_8$ and $R_9$, $R_{11}$ and $R_{12}$ may form, respectively, with the carbon atoms that bear them, an optionally substituted aryl ring, preferably phenyl.

In accordance with another embodiment, $R_2$, $R_3$, $R_5$, $R_6$, $R_8$, $R_9$, $R_{11}$ and $R_{12}$ may represent a hydrogen atom.

Preferably, $R_1$, $R_4$, $R_7$ and $R_{10}$, which may be identical or different, represent an optionally substituted pyridinium group; a phenyl group substituted with a sulfonate group $SO_3M'$-; a linear or branched $C_8$-$C_{30}$ alkyl radical which may be interrupted with one or more heteroatoms and/or which may be substituted.

According to one embodiment, $R_1$, $R_4$, $R_7$ and $R_{10}$ represent an optionally substituted pyridinium group.

According to another embodiment, $R_1$, $R_4$, $R_7$ and $R_{10}$ represent a phenyl group substituted with a group $SO_3M'$.

According to another embodiment, $R_1$, $R_4$, $R_7$ and $R_{10}$ represent a linear or branched $C_8$-$C_{30}$ and in particular $C_8$-$C_{18}$ alkyl radical which may be interrupted with one or more groups containing heteroatoms and/or which may be substituted.

In particular, $R_1$, $R_4$, $R_7$ and $R_{10}$ represent a $C_8$, $C_{12}$ or $C_{18}$ alkyl radical.

Preferentially, $R_1$, $R_4$, $R_7$ and $R_{10}$ represent a pyridinium group, which is in particular unsubstituted.

In accordance with a particular embodiment, M is chosen from transition metals and $R_2$, $R_3$, $R_5$, $R_6$, $R_8$, $R_9$, $R_{11}$ and $R_{12}$ represent a hydrogen atom.

Even more preferentially, M is chosen from transition metals, especially zinc (Zn), $R_2$, $R_3$, $R_5$, $R_6$, $R_8$, $R_9$, $R_{11}$ and $R_{12}$ represent a hydrogen atom, and $R_1$, $R_4$, $R_7$ and $R_{10}$ represent an optionally substituted pyridinium group.

Preferably, the compound of formula (I) used in the context of the present invention is the following compound:

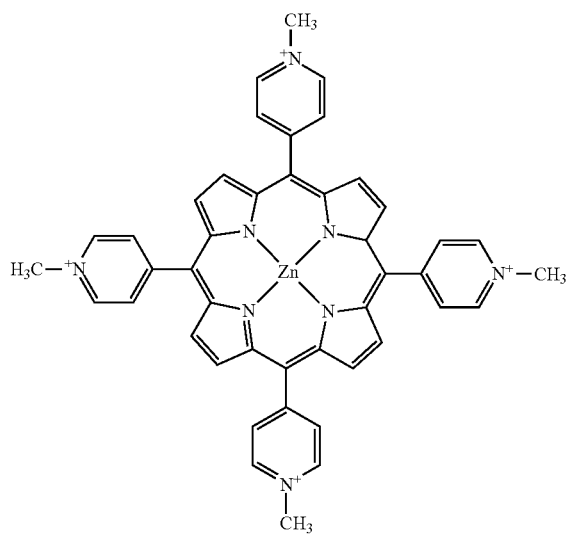

The catalytic oxidation compound, alone or as a mixture, may be present in the cosmetic composition in a content ranging from 0.0001% to 1% by weight, preferably in a content ranging from 0.001% to 0.5% by weight and more particularly in a content ranging from 0.01% to 0.1% by weight relative to the total weight of the cosmetic composition.

A mixture of catalytic oxidation compounds of formula (I) may, of course, be used. Thus, the cosmetic composition may comprise two or more different catalytic oxidation porphyrin compounds as defined in formula (I).

In particular, the cosmetic composition may comprise two or more different catalytic oxidation porphyrin compounds (I), chosen from:
  cationic catalytic oxidation porphyrin compounds,
  anionic catalytic oxidation porphyrin compounds and
  nonionic catalytic oxidation porphyrin compounds comprising one or more fatty chains;
  and mixtures thereof.

The term "fatty chain" means a hydrocarbon-based chain comprising at least 8 carbon atoms, especially from 8 to 30 carbon atoms and more particularly from 8 to 18 carbon atoms.

According to a first embodiment, the cosmetic composition may comprise one or more cationic catalytic oxidation porphyrin compounds of formula (I) and one or more anionic catalytic oxidation porphyrin compounds of formula (I)

In particular, the cosmetic composition may comprise a cationic catalytic oxidation porphyrin compound of formula (I) in which $R_1$, $R_4$, $R_7$ and $R_{10}$ represent an optionally substituted pyridinium group and an anionic catalytic oxidation porphyrin compound of formula (I) in which $R_1$, $R_4$, $R_7$ and $R_{10}$ represent a phenyl group substituted with a group $SO_3M'$-.

According to a second embodiment, the cosmetic composition may comprise one or more cationic catalytic oxidation porphyrin compounds of formula (I) and one or more nonionic catalytic oxidation porphyrin compounds comprising one or more fatty chains of formula (I).

In particular, the cosmetic composition may comprise a cationic catalytic oxidation porphyrin compound of formula (I) in which $R_1$, $R_4$, $R_7$ and $R_{10}$ represent an optionally substituted pyridinium group and a nonionic catalytic oxidation porphyrin compound of formula (I) in which $R_1$, $R_4$, $R_7$ and $R_{10}$ represent a $C_8$-$C_{30}$, especially $C_8$-$C_{18}$ and in particular $C_8$, $C_{12}$ and $C_{18}$ alkyl radical.

According to a third embodiment, the cosmetic composition may comprise one or more anionic catalytic oxidation porphyrin compounds of formula (I) and one or more nonionic catalytic oxidation porphyrin compounds comprising one or more fatty chains of formula (I).

In particular, the cosmetic composition may comprise an anionic catalytic oxidation porphyrin compound of formula (I) in which $R_1$, $R_4$, $R_7$ and $R_{10}$ represent a phenyl group substituted with a group $SO_3M'$- and a nonionic catalytic oxidation porphyrin compound of formula (I) in which $R_1$, $R_4$, $R_7$ and $R_{10}$ represent a $C_8$-$C_{30}$, especially $C_8$-$C_{18}$ and in particular $C_8$, $C_{12}$ and $C_{18}$ alkyl radical.

The compounds of formula (I) according to the invention may be readily prepared by a person skilled in the art on the basis of his general knowledge.

The cosmetic compositions that may be used in the context of the invention generally comprise a cosmetically acceptable medium, i.e. a medium that is compatible with keratin materials such as the skin of the face or of the body, the hair, the eyelashes, the eyebrows and the nails.

The compounds according to the invention are generally used in topical application. In particular, they may be used as antidandruff agents in a cosmetic composition that may be in any galenical form normally used for topical application.

The cosmetic composition used according to the invention may be a rinse-out or leave-in composition. The said composition, especially a hair composition, is preferably a shampoo, a cream, a mousse (aerosol or non-aerosol), a paste, a gel, an emulsion, a lotion or a stick. Preferably, the cosmetic composition is a shampoo, a gel or a lotion.

The cosmetic composition may be anhydrous or may comprise, preferably, an aqueous or aqueous-organic medium; it may thus comprise water and/or one or more organic solvents that may be chosen from linear or branched C1-C6 monoalcohols such as ethanol, isopropanol, tert-butanol or n-butanol; polyols such as glycerol, propylene glycol, hexylene glycol (or 2-methyl-2,4-pentanediol), and polyethylene glycols; polyol ethers such as dipropylene glycol monomethyl ether; and mixtures thereof.

Preferably, the cosmetic composition comprises an amount of organic solvents ranging from 0.05% to 60%, preferably from 0.5% to 50% and better still from 1% to 40% by weight, relative to the total weight of the cosmetic composition.

The cosmetic composition may also advantageously comprise at least one additional constituent that is common in cosmetics, especially such as thickeners; surfactants chosen from anionic, cationic, nonionic, amphoteric and/or zwitterionic surfactants; conditioning agents; silicones; hair-loss counteractants; other antidandruff agents; vitamins; waxes, sunscreens, mineral or organic, coloured or uncoloured pigments; dyes; nacreous agents and opacifiers, sequestrants, plasticizers, fragrances; preserving agents. Needless to say, a person skilled in the art will take care to select this or these optional additional compound(s), and/or the amount thereof, such that the advantageous properties of the composition according to the invention are not, or are not substantially, adversely affected by the envisaged addition.

Most particularly, the cosmetic composition may comprise one or more oxidizing agents chosen especially, for example, from hydrogen peroxide, urea peroxide, alkali metal bromates, persalts such as perborates and persulfates, and enzymes such as peroxidases and two-electron or four-electron oxidoreductases.

Most particularly, the cosmetic composition may comprise one or more polymers, in particular those described in the article "Novel Porphyrin—Incorporated Hydrogels for Photoactive Intraocular Lens Biomaterials", Journal of Physical Chemistry B (2007), 111(3), 527-534.

Preferably, the cosmetic composition does not comprise (0%) any sequestrants, especially sequestrants that are capable of taking up the metal from the catalytic oxidation compounds of formula (I).

Preferably, the cosmetic composition comprises one or more sequestrants in a small content, in particular in a content of less than 1% by weight and more particularly less than 0.01% by weight relative to the total weight of the composition.

Preferably, the cosmetic composition may comprise one or more particles bearing a cationic or anionic surface charge. In particular, the cosmetic composition may comprise one or more particles bearing an ionic surface charge opposite to that of the catalytic oxidation compounds according to the invention. More particularly, the cosmetic composition may comprise one or more particles bearing an ionic surface charge opposite to that of the catalytic oxidation porphyrin compounds according to the invention. Thus, the cosmetic composition may comprise one or more cationic porphyrin compounds as defined previously and one or more particles bearing an anionic surface charge. Similarly, the cosmetic composition may comprise one or more anionic porphyrin compounds as defined previously and one or more particles bearing a cationic surface charge. The particles may be mineral or organic. Among the mineral particles, mention may be made of clays, silicates, silica, kaolin, hydroxyapatite or particles formed by alkaline-earth metals, transition metals, rare-earth metals and alloys of these metals. In particular, the particles may be silica and alumina.

According to one embodiment, the cosmetic composition may be aqueous. The term "aqueous" refers to a composition whose free water content is greater than 10% by weight, preferably greater than 30% by weight, better still greater than 50% by weight and even better still greater than 70% by weight relative to the total weight of the composition.

According to another embodiment, the cosmetic composition may be anhydrous. The term "anhydrous" refers to a composition whose content of free or added water is less than 10% by weight and especially 3% by weight, and preferably whose content of added water is less than 1% by weight relative to the total weight of the composition. Preferably, the anhydrous cosmetic composition does not contain any water. In particular, the cosmetic composition may be anhydrous in the case where the catalytic oxidation compounds comprise in their structure one or more fatty chains.

The cosmetic composition may or may not be rinsed out after having been applied to the keratin materials (hair and/or scalp).

According to one variant of the invention, prior to the application of the cosmetic composition according to the invention to keratin materials, a cosmetic composition for preparing the surface of the said keratin materials may be applied; such a "preparation" composition may make it possible to improve the retention of the porphyrin, phthalocyanin and/or porphyrazine catalytic oxidation compound especially on rinsing and washing. In particular, the preparation composition makes it possible to improve the retention of the porphyrin compound, especially on rinsing and washing.

Preferably, the step of preparing the surface of the keratin materials consists in applying to the said surface a cosmetic composition comprising, in a cosmetically acceptable medium, one or more reducing compounds.

According to another variant of the invention, after application of the cosmetic composition according to the invention to the keratin materials, a cosmetic composition for conserving the hold of the catalytic oxidation compounds on the surface of the said keratin materials may be applied. Preferably, a cosmetic composition comprising one or more polymers in a cosmetically acceptable medium is applied to the said keratin materials; this composition may make it possible to retain efficiently the catalytic oxidation compounds on the surface of the keratin material.

Moreover, after application of the cosmetic composition according to the invention, a composition comprising one or more active agents chosen from antibacterial agents, antifungal agents and/or powders may be applied to the surface of the keratin materials.

It is also possible to apply, before or after the application of the composition according to the invention, a cosmetic composition comprising one or more oxidizing agents. Alternatively, a cosmetic composition comprising, in a cosmetically acceptable medium, one or more compounds capable of releasing one or more oxidizing agents, may also be applied. By way of example, the said cosmetic composition may contain a mixture comprising glucose oxidase and glucose.

A further subject of the invention is a cosmetic treatment process for eliminating and/or reducing dandruff, especially that caused by yeasts of the *Malassezia* genus, characterized in that it comprises the application, to the hair and/or the scalp, of at least one catalytic oxidation compound chosen from porphyrins, phthalocyanins and porphyrazines, and mixtures thereof, or alternatively a cosmetic composition comprising the same.

The application of the catalytic oxidation compound(s), or of the composition comprising the same, may optionally be followed by a step of rinsing with water.

Preferably, this cosmetic treatment process is repeated at least twice a week.

According to one embodiment, the cosmetic treatment process may comprise the following steps:
 a cosmetic composition comprising, in a cosmetically acceptable medium, one or more cationic catalytic oxidation porphyrin compounds as defined previously is applied to the keratin materials,
 a cosmetic composition comprising, in a cosmetically acceptable medium, one or more anionic catalytic oxidation porphyrin compounds as defined previously is applied to the said keratin materials.

In accordance with this embodiment, the cosmetic composition comprising the anionic catalytic oxidation porphyrin compound may or may not be applied immediately after the cosmetic composition comprising the cationic catalytic oxidation porphyrin compound (or vice versa).

According to another embodiment, the cosmetic treatment process may comprise the following steps:
 a cosmetic composition comprising, in a cosmetically acceptable medium, one or more cationic catalytic oxidation porphyrin compounds as defined previously is applied to the keratin materials, and
 a cosmetic composition comprising, in a cosmetically acceptable medium, one or more nonionic catalytic oxidation porphyrin compounds comprising one or more fatty chains as defined previously is applied to the said keratin materials.

In accordance with this embodiment, the cosmetic composition comprising the nonionic catalytic oxidation porphyrin compound containing one or more fatty chains may or may not be applied immediately after the cosmetic composition comprising the anionic catalytic oxidation porphyrin compound (or vice versa).

According to another embodiment, the cosmetic treatment process may comprise the following steps:
 a cosmetic composition comprising, in a cosmetically acceptable medium, one or more anionic catalytic oxidation porphyrin compounds as defined previously is applied to the keratin materials, and
 a cosmetic composition comprising, in a cosmetically acceptable medium, one or more nonionic catalytic oxidation porphyrin compounds comprising one or more fatty chains as defined previously is applied to the said keratin materials.

In accordance with this embodiment, the cosmetic composition comprising the nonionic catalytic oxidation porphyrin compound containing one or more fatty chains may or may not be applied immediately after the cosmetic composition comprising the anionic catalytic oxidation porphyrin compound (or vice versa).

The invention is illustrated in greater detail in the examples that follow.

EXAMPLE 1

Compound Tested

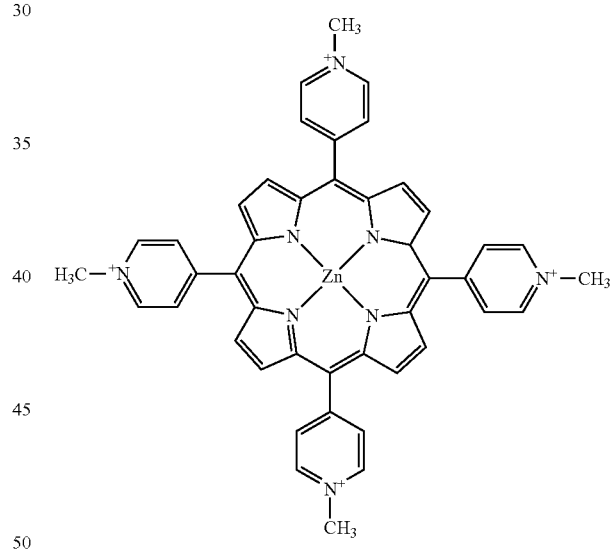

This porphyrin compound responds positively especially to tests 1 and 2 as described above.

The inhibitory activity of this compound with respect to *Malassezia furfur* was evaluated in the following manner.

The test is performed using a micro-method developed on a microplate. The test principle is based on placing decreasing concentrations of compound in contact with an identical inoculum of microorganisms in a culture medium suitable for the growth thereof.

The test compound is thus placed in contact with an inoculum of the microorganism, in a culture medium suitable for its growth (Sabouraud medium with 10% olive oil).

After incubation for 24 to 48 hours, at 32.5° C., the optical density (620 nm) is measured and the results are expressed as a percentage of growth calculated relative to a growth control (not comprising the test compound).

Dilutions of the compound are prepared in agar to 1/1000; each concentration is tested three times.

It is found that at a concentration of 0.001% by weight of test compound, eradication of the *Malassezia furfur* microorganisms is obtained (reduction by a factor of greater than 10 000).

The invention claimed is:

1. A method for eliminating and/or reducing dandruff, the method comprising:
applying to the hair and/or the scalp a cosmetic composition comprising at least one catalytic oxidation compound chosen from the compounds of formula (II):

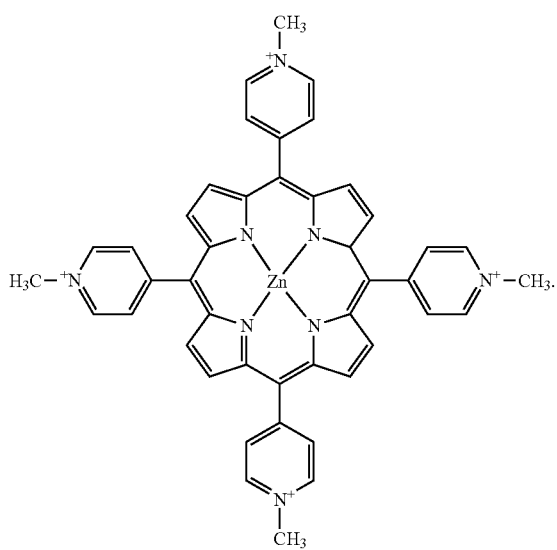

(II)

2. The method according to claim 1, further comprising applying a preparation composition to the hair and/or scalp for preparing a surface of the hair and/or scalp prior to applying the cosmetic composition.

3. The method according to claim 1, further comprising applying a holding composition to the hair and/or scalp for conserving the hold of the catalytic oxidation compounds on a surface of the hair and/or scalp after applying the cosmetic composition.

4. The method according to claim 3, wherein the holding composition comprises at least one polymer.

5. The method according to claim 1, wherein the cosmetic composition comprises two or more different catalytic oxidation porphyrin compounds chosen from:
cationic catalytic oxidation porphyrin compounds,
anionic catalytic oxidation porphyrin compounds,
nonionic catalytic oxidation porphyrin compounds comprising one or more fatty chains, and
mixtures thereof.

6. The method according to claim 1, wherein the cosmetic composition further comprises at least one additional constituent chosen from water;
organic solvents; thickeners; surfactants; conditioning agents; silicones; hair-loss counteractants; other anti-dandruff agents; vitamins; waxes; sunscreens; mineral or organic, coloured or uncoloured pigments; dyes; nacreous agents and opacifiers; sequestrants;
plasticizers; fragrances; preserving agents; oxidizing agents; polymers; and particles bearing a cationic or anionic surface charge.

7. The method according to claim 6, wherein the surfactant is chosen from anionic, cationic, nonionic, amphoteric and/or zwitterionic surfactants.

8. The method according to claim 1, wherein the at least one catalytic oxidation compound is present in the cosmetic composition in an amount ranging from about 0.0001% to about 0.001% by weight, relative to the total weight of the cosmetic composition.

* * * * *